United States Patent [19]

Martin et al.

[11] Patent Number: 5,583,284

[45] Date of Patent: Dec. 10, 1996

[54] METHOD FOR MONITORING GREASE CONSISTENCY

[75] Inventors: David N. Martin, Royal Oak; James F. Van Auken, Riverview, both of Mich.

[73] Assignee: Mobil Oil Corporation, Fairfax, Va.

[21] Appl. No.: 304,966

[22] Filed: Sep. 13, 1994

[51] Int. Cl.$^6$ ............................ G01N 11/04; G01N 11/08
[52] U.S. Cl. ...................... 73/54.09; 73/54.04; 73/54.11; 73/54.14
[58] Field of Search ............................... 73/54.09, 54.01, 73/54.02, 54.04, 54.11, 54.14

[56] References Cited

U.S. PATENT DOCUMENTS

| | | | |
|---|---|---|---|
| 1,586,948 | 6/1926 | Connet | 73/54.09 |
| 2,459,483 | 1/1949 | Zimmer et al. | 73/54.09 |
| 3,116,630 | 1/1964 | Piros | 73/54.04 |
| 3,302,451 | 2/1967 | Martin | 73/54.04 |
| 3,468,158 | 9/1969 | Chien | 73/54.09 |
| 3,475,335 | 10/1969 | Greene et al. | 252/39 |
| 4,043,183 | 8/1977 | Higgs et al. | 73/54.29 |
| 4,297,227 | 10/1981 | Witte et al. | 252/18 |
| 4,442,704 | 4/1984 | Swearingen | 73/54.09 |
| 4,444,669 | 4/1984 | Wittse, Jr. et al. | 252/41 |
| 4,495,798 | 1/1985 | Ehrgott | 73/54.01 |
| 5,272,912 | 12/1993 | Katsuzaki | 73/54.09 |

FOREIGN PATENT DOCUMENTS 129239  1/1978  Germany .............................. 73/54.04

OTHER PUBLICATIONS

Boner, C. J., "Manufacture and Application of Lubricating Greases", Reinhold Publishing Corp. 1954, pp. 823–825 and 834–835.
Wills, J. G., "Lubrication Fundamentals", Marcel Dekker, Inc., 1980, pp. 64–68.
Standard Test Methods For Cone Penetration of Lubricating Grease, ASTM Designation D 217–82, 1982, pp. 141–152.

*Primary Examiner*—Hezron E. Williams
*Assistant Examiner*—Daniel S. Larkin
*Attorney, Agent, or Firm*—Ronald A. Bleeker; Malcolm D. Keen

[57] ABSTRACT

The invention relates to continuous grease making processes. The invention further relates a method for monitoring the consistency of the final product stream of a continuous grease making process. The finished product is passed through a venturi where a pressure drop occurs as the grease moves therethrough. The observed pressure drop is then corrected to ideal conditions based on temperature, flow rate and venturi size. The resulting adjusted pressure drop can then be correlated via an emperically derived realtionship to the consistency of the grease.

11 Claims, 3 Drawing Sheets

METHOD FOR MONITORING GREASE CONSISTENCY

FIELD OF THE INVENTION

The invention relates to the manufacture of lubricating greases using a continuous process. The invention further relates to a method for continuously monitoring the consistency of the finished grease product by correlating the product pressure drop across a venturi to the consistency of the finished grease. Monitoring the pressure drop allows operators of the continuous grease process to monitor product quality and quickly detect any problems with the ongoing grease production.

BACKGROUND OF THE INVENTION

The present invention relates to a method for monitoring the consistency of the grease manufactured by a continuous grease making process. Continuous grease making processes were developed in the early 1960's. Their refinement has been vigorously pursued due to the potential advantages the continuous process offers over the widely used batch process for grease manufacture. Some understanding of the batch process is required in order to fully appreciate the advantages of the continuous grease making process. The batch method is currently the most widely used method for grease making. Batch processing is carried out with equipment having widely varying capacities. That capacity can range from 50 pounds of grease to about 20,000 pounds of grease. The equipment involved can be expansive taking up two floors of a building and employing a large operating crew. The major components of a typical batch process are a contactor, a kettle, and various kinds of finishing equipment. The contactor is a pressure vessel wherein the thickener that provides the structure to hold the lubricating oil contained in the grease is formed. The thickener most commonly used for modern grease production is some sort of metallic soap made from a fatty acid, a metal base, water, and in some cases a small amount of lubricating oil. The soap is usually referred to by the name of the metal base used to make the soap. Commonly used metals used include aluminum, lithium and barium. These components undergo a saponification process whereby they are mixed in the presence of heat and pressure to form the soap thickener. Greases referred to as complex greases were developed when it was discovered that different kinds of fats could be combined to make greases. As the art of grease making has evolved over the years, the term complex grease has been used for many different purposes but today has generally been accepted to refer to a high temperature application grease.

From the contactor the soap mixture is transferred to a kettle for dehydration and the addition of additional oil stock. The soap structure leaving the contactor is quite wet and as in any grease manufacturing process requires removal of excess water. The soap mixture will remain in the kettle for many hours where the mixture is heated and water vapor is drawn therefrom. The kettles typically contain internal agitators or scrapers that serve to break up the soap structure to improve the consistency and workability of the grease. The scrapers also remove masses of soap from the sides of the kettle. The kettles are heated by steam, electricity or via the circulation of some type of hot oil. The type of heat source utilized will vary with the maximum temperature required in order to form the grease.

From the kettle the grease is pumped to various kinds of finishing equipment. This finishing equipment is required to ensure that the soap structure and any grease additives are evenly distributed throughout the grease. This equipment includes milling machines which break up the fibrous structure of the soap and homogenizers which improve the dispersion of the soap in the grease. The finishing step could also include filtration to remove impurities or deaeration to remove entrained air. Air is introduced into the grease while it is beaten in the kettle. Excess air can cause problems with the appearance of the grease and can prevent the required weight of grease from being introduced into the intended packages. The grease is then cooled and packaged.

A number of variations on the batch process are possible to include changing the size of the kettle used and carrying out the entire process inside one vessel. However, a common characteristic of all batch processes is that the grease is manufactured in discrete units in a discontinuous fashion.

By contrast continuous grease production units take up a fraction of the space required by batch processing equipment and can be operated by a small complement of operators. The continuous production process has proven capable of achieving a higher output of a consistently high quality product. Moreover, this process results in less wasted product created during the changeover from one grease to another.

An early continuous grease production method was described in U.S. Pat. No. 3,475,335 to Greene et al. That process comprised continuously introducing a saponifiable material and a metal base into a tubular reaction zone at high temperature and pressure under turbulent conditions to obtain substantially complete reaction. Next a lubricating oil is introduced into the product stream that is continuously withdrawn from the reaction zone. The product stream continues to a dehydration zone wherein the grease mixture is maintained at an elevated temperature but below the melting point of the soap and under a pressure substantially lower than the pressure in the reaction zone. The grease is maintained in the dehydration zone for a period sufficient to substantially dehydrate the mixture. The product stream out of the dehydration zone is partially recycled back into that zone through a shear valve which serves to condition the soap fibers contained in the grease. The product stream is then additized and passed to coolers and possibly through additional conditioning steps.

U.S. Pat. No. 4,297,227 to Witte et al. describes an improvement to a continuous grease making process which permits the use of water soluble additives in grease compositions. The improvement permits the incorporation of such additives in an evenly dispersed fashion thereby eliminating the need for a separate step to form an additive slurry. In this improved process a saponifiable material and a metal base are continuously introduced at elevated temperatures and superatmospheric pressure into a saponification zone where they are saponified under turbulent conditions. The saponified product is then mixed with an aqueous solution of water soluble additive materials at superatmospheric pressure sufficient for maintaining all water in the liquid phase. The product is then dehydrated by flash vaporizing substantially all the water therefrom. The resulting grease has a water soluble additive evenly dispersed therethrough as particles not exceeding about 10 microns in size.

A process for the continuous production of high dropping point lithium complex soap greases is disclosed in U.S. Pat. No. 4,444,669 to Wittse, Jr. et al. The thickener used in that invention is a mixture of lithium soaps of hydroxy monocarboxylic fatty acids and dicarboxylic fatty acids. The patent notes that process conditions must be very closely controlled in order to produce the desired high dropping point greases.

As stated herein above, a critical requirement for the successful utilization of continuous grease processes has been the need to monitor product quality during production. The high production rates possible with these units creates the possibility that a large amount of off-specification product can be produced between the time that a problem is detected and the time that production is shut down. Monitoring is particularly important during start up of the operation. During the time required for adjustment and stabilization of grease flow a great deal of unusable product may be produced. Such a large volume of unusable product can make the continuous process an extremely uneconomic venture. Therefore it is critical to be able to monitor the quality of the effluent stream of a continuous grease production unit to determine the instant when the transition from unacceptable to acceptable product occurs.

The parameter most often monitored is the grease consistency. This term has been used to refer to the texture or elasticity of a grease, however, it is now accepted to refer to the degree to which a grease will deform upon the application of a force. Consistency is measured using the cone penetration test specified in ASTM D217, "Cone Penetration of Lubricating Grease." The test is conducted using an ASTM penetrometer and is widely known by skilled operators. Accordingly the details of the test procedure will not be repeated here. The test is simple easy to conduct and provides reproducible results. Test results are reported in the number of tenths of millimeters to which a standard cone sinks into a grease under prescribed conditions. As the penetration number increases so does the softness of the grease. In the context of a continuous grease process, however, the test requires a great deal of time to conduct. Quite a large volume of unusable grease can be produced during the time required to take a sample and perform the penetrometer test. Accordingly if grease will be made by a continuous process, it must be monitored by a continuous process.

An apparatus for the continuous monitoring the consistency of a lubricating grease stream is disclosed in U.S. Pat. No. 4,043,183 to Higgs et al. That consistometer included a resilient member located in the stream of material and a reference member located outside of the stream. Both members rotate synchronously and are spatially related to sensors that detect the passage of the members. The reference member and resilient member generate reference and resilient pulses respectively which signals are fed to a network that provides an output corresponding to the consistency of the material.

While this consistometer performed adequately for simple greases, it has been found that certain types of polymeric additives used in complex greases cause the consistometer to give inaccurate readings. Those additives caused the grease to adhere very strongly to the resilient rotating member resulting in inaccurate outputs. Without accurate, timely information on the consistency of the grease as it is being produced, quite a bit of guess work is required to use the continuous process. As a result, an economically unacceptable amount of off-specification grease would be produced unless the manual penetrometer test described herein above is performed. Therefore, there exists a need for a reliable means to monitor the consistency of the effluent stream of a grease making process.

SUMMARY OF THE INVENTION

The present invention relates to a method of monitoring the consistency of a lubricating grease comprising the steps of passing the grease process stream through a venturi so that a pressure drop occurs; measuring the pressure drop using two axially separated pressure tap points along the venturi; and correlating the pressure drop to the consistency of the lubricating grease. In this method the pressure drop occurs at a constant temperature, flow rate and pressure into the venturi. The pressure drop is adjusted to ideal temperature and flow rate conditions according to the relationship $$\Delta P_{adj} = \Delta P + X_1(78+T) + X_2(R-100)$$

where $\Delta P_{adj}$ is the adjusted pressure drop, $\Delta P$ is the observed pressure drop, T is grease temperature, R is flow rate and $X_1$ and $X_2$ are production factors associated with a certain size venturi.

The method also relates to converting the adjusted pressure drop to an electronic signal which is proportional to the pressure drop. The electronic signal may be displayed on a digital display. Another aspect of the present invention is to monitor the signal electronically for variation beyond a predetermined range. When the signal leaves that range an alarm would be actuated to alert operators to take steps to correct the alarm condition.

The method of the present invention provides many advantages. It permits the continuous production of complex greases meeting desired consistency specifications much sooner after coming on line than was possible with prior art methods. Accordingly, it results in the production of a minimal amount of grease that must be reworked or recycled before acceptable quality product is produced.

Therefore it is an object of this invention to provide a method for continuously monitoring the consistency of the final product of a continuous grease making process.

It is another object of this invention to greatly reduce the amount of off-specification grease produced during the start up of a continuous grease making unit.

It is still another object of this invention to provide a means to alert the operators of a continuous grease making process to the fact that system parameters are outside allowable limits.

The foregoing and other objects, features and advantages of the invention will be better understood from the following more detailed description and appended claims.

DETAILED DESCRIPTION OF THE INVENTION

Figure 1:
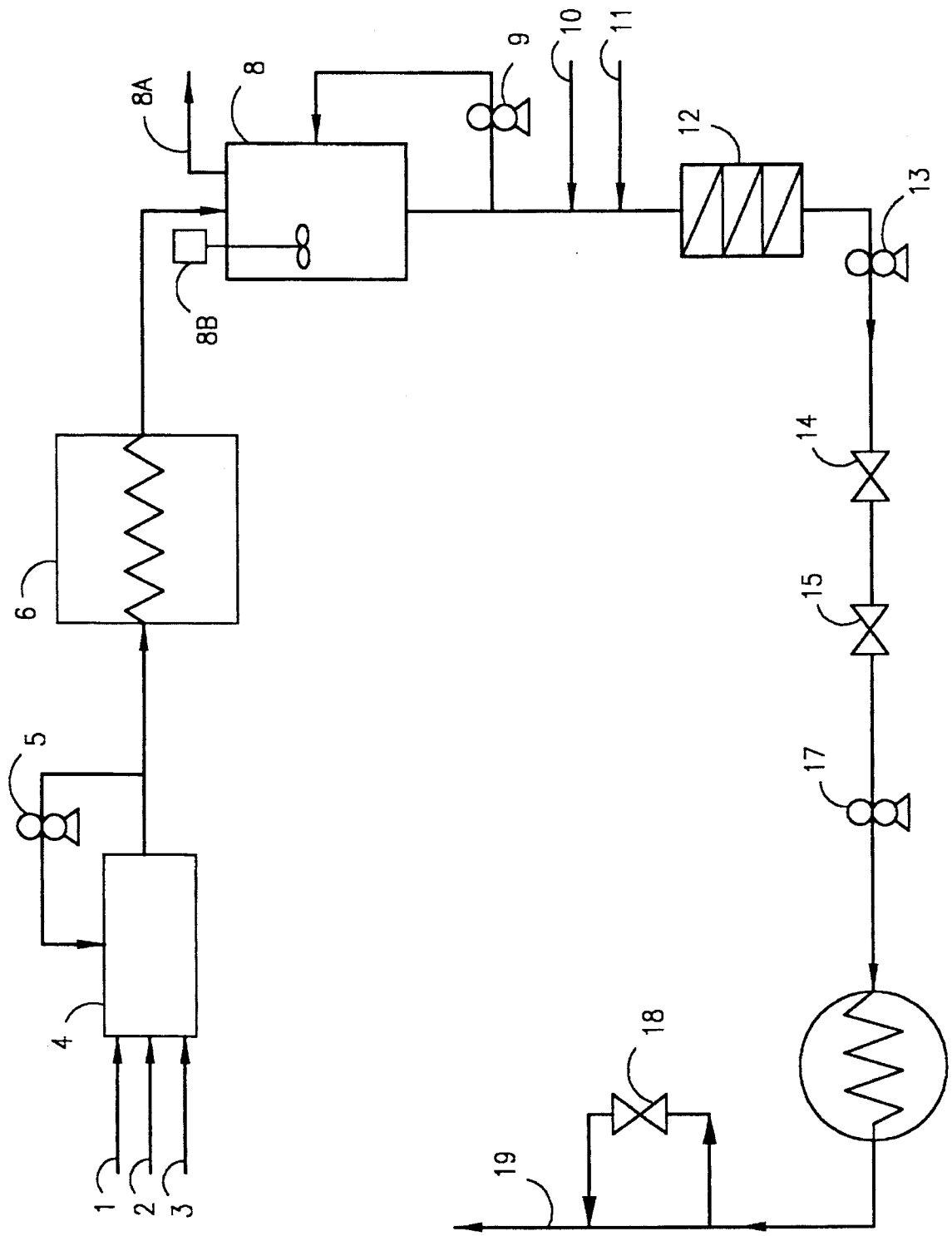
FIG. 1 is a schematic of a typical continuous grease making process.

Attention is directed to FIG. 1 where a continuous grease making process incorporating the present invention is illustrated in simplified form. The process is initiated in a reactor 4 where three inputs are heated and mixed under turbulent conditions. The inputs are lubricating oil 1, alkali 2 and a fat 3. The saponification or soap forming step described herein above takes place in the reactor which is maintained at a superatmospheric pressure and at a temperature consistent with the desired final product. A portion of the output of the reactor is recycled via pump 5 back into the reactor so as to maintain a high flow rate through the reactor. The recycling also speeds the mixing process of the inputs therein. The product of the saponification reaction then passes through a soap base heater 6 to a flash chamber 8. The flash chamber is also known as a dehydration chamber. In the flash chamber two events take place. First, the soap base is dehydrated of the moisture formed as a result of the saponification process. The dehydration takes place under subatmospheric conditions. The resulting water vapor is drawn off at 8A. Second, the soap base is conditioned by the recycling of the flash chamber output by pump 9. It is also typical to agitate the flash chamber mixture with agitator 8B. The temperature maintained in the flash chamber and the residence time of the soap base in the flash chamber (controlled by the amount of recycling) can vary widely with the type of grease being made. After the soap base leaves the flash chamber it is blended in-line with additives represented by 10 and additional oil 11. The mixture is then passed through a static mixer 12 which conditions and ensures adequate dispersion of the additives therein. The rough grease thus formed then goes through a final finishing section pump 13 and on to a series of shear valves 14, 15. The grease undergoes a pressure drop and shearing action in the valves to improve soap and additive dispersion. The shear valves also give the grease its final smooth appearance. From the finishing section the now final grease process stream grease is pumped by booster pump 17 to the consistency monitoring venturi 18 where a pressure drop occurs. This pressure drop is correlated to the consistency of the final grease stream 19 as described herein below.

Figure 2:
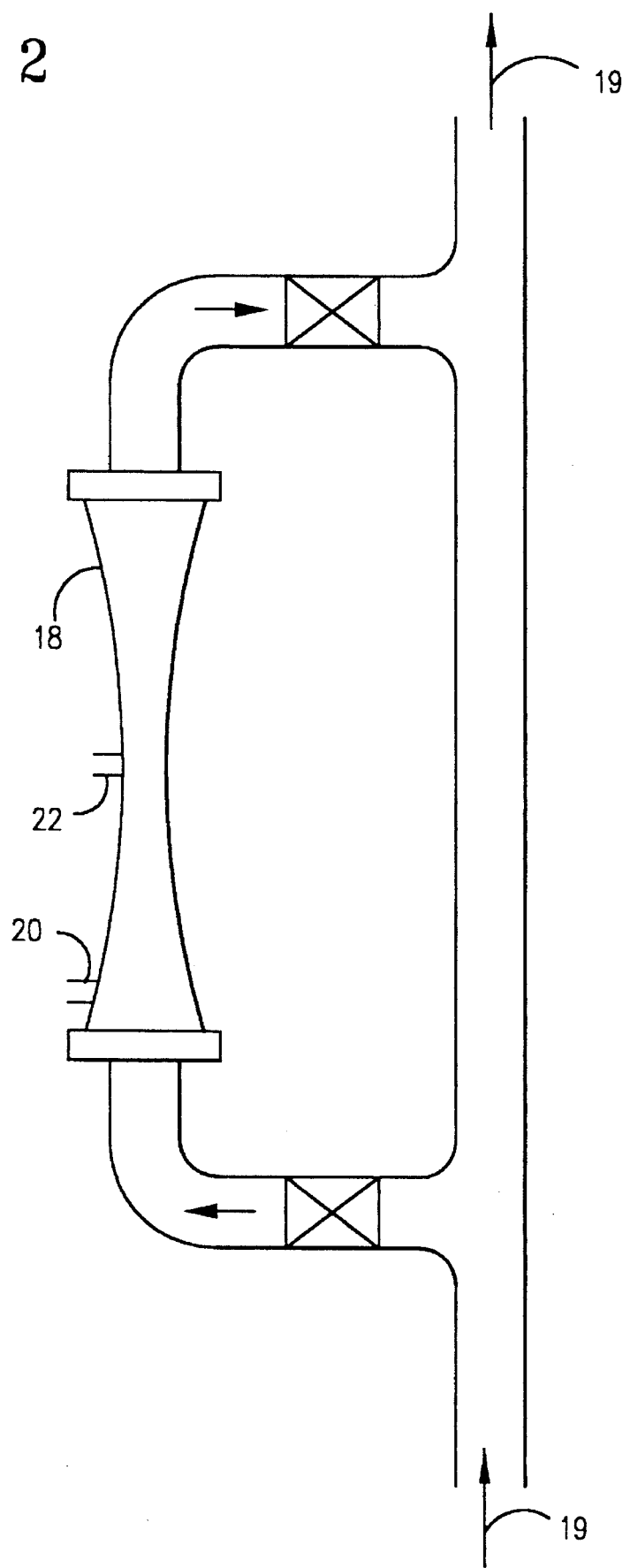
FIG. 2 is a schematic representation of the present invention.

Turning now to FIG. 2, it can be seen that the venturi 18 is positioned in the line carrying the final product stream 19. The venturi 18 is provided with two pressure tap points 20, 22 which are axially separated along its length. The pressure drop that occurs in the venturi can be measured by comparing the observed pressures at the two tap points. That pressure differential can then be converted by appropriate electronic computing means to a pressure drop reading given in inches of water. The venturi must be positioned in the process so as to ensure that the pressure drop occurs at a constant temperature, flow rate, and pressure into the venturi. Each of these parameters will vary with the particular product being produced but will remain essentially constant during the production of any one product.

A venturi offers many advantages as a device to create a measurable pressure drop for the purposes of the instant invention. First, a venturi is manufactured to much closer tolerances than standard seamless pipe which could be used for this purpose. This characteristic provides for repeatability and consistency of measurement from installation to installation. Second, the design of a venturi is such that a pressure drop is developed in a relatively short length of piping. Thus its use in space-constrained plant environments is quite beneficial. Moreover, the open flow design of a venturi avoids the problems encountered with the prior art consistometers described herein above relating to the adverse effects of polymeric additives on rotating members. Those additives improve the tackiness or ability of the grease to adhere to a metal surface in actual service use. However for the purposes of flow through a measuring type device that tackiness can be an impediment to accurate measurement.

Modeling of the pressure drop that occurs in a venturi when a newtonian fluid is passed therethrough is well known. However, to the extent that it behaves as a fluid, grease is non-newtonian. Therefore, a relationship between pressure drop and the consistency of complex greases was developed empirically. That relationship is illustrated graphically in FIG. 3. The two curves shown in FIG. 3 describe the correlation between pressure drop through the venturi and consistency. Curve A is for greases containing molybdenum or polymeric additives. Curve B is for non molybdenum/polymeric additized greases. The horizontal axis shows the adjusted pressure drop or $\Delta P_{adj}$ in inches of water. The vertical axis shows worked grease consistency as measured by ASTM D217. The adjusted pressure drop used for this correlation was developed empirically and is given by the relationship $$\Delta P_{adj} = \Delta P + X_1(78+T) + X_2(R-100)$$

where
$\Delta P$ is the observed differential pressure drop across the venturi
T is the finished product temperature in degrees Fahrenheit
R is the production flow rate in pounds/min
$X_1$ and $X_2$ are temperature and flow rate factors respectively This adjusted pressure drop is the observed pressure drop adjusted for the difference between actual system conditions at the instant a measurement is taken and ideal design condition of 100 pounds/min flow rate and production temperature. The factors $X_1$ and $X_2$ are related to venturi size. They must be determined anew in the event a different venturi is to be used.

During the development of the instant invention, it was found that below a certain size, the venturi would actually shear the grease so as to adversely effect the soap structure therein and the properties of the finished product. Therefore, sizing the venturi is important to the successful practice of the present invention and must take into consideration anticipated production temperature and flow rates. Preferably a venturi size of 3 inches or less should be used. Most preferable is a venturi size of about 1½ inches. For a given grease production run an essentially constant temperature, pressure and flow rate must be maintained into the venturi to provide stable, accurate, and repeatable results. Only after the completion of the last of the finishing steps is the grease in a relatively steady state condition so as to permit accurate monitoring. By steady state condition it is meant that no wide fluctuations of temperature, pressure or flow rate take place.

Although the present invention has been described with the use of a manual correlation process, it is easily adaptable to automatic operation and control of the continuous grease making process. It can also be converted into an electronic signal proportional to the pressure drop through the venturi. That signal can be converted to a digital display so as to be continuously monitored by operators either by a local display unit or remotely via a microcomputer. Alternatively, the signal can be monitored remotely by a microcomputer means for variation from a predetermined range so that a pressure drop variation outside that range would actuate an alarm to alert operators to the problem condition, thus permitting corrective measures to be taken. Conceivably the alarm condition could trigger the shut down of the continuous grease making process. However, it would be more economical given the nature of the continuous nature of this process to divert the off-specification product stream to a holding tank until the alarm condition could be corrected.

Abrupt system shut downs should be avoided as they result in the formation of congealed, difficult to remove soap, oil and grease components in system piping.

Figure 3:
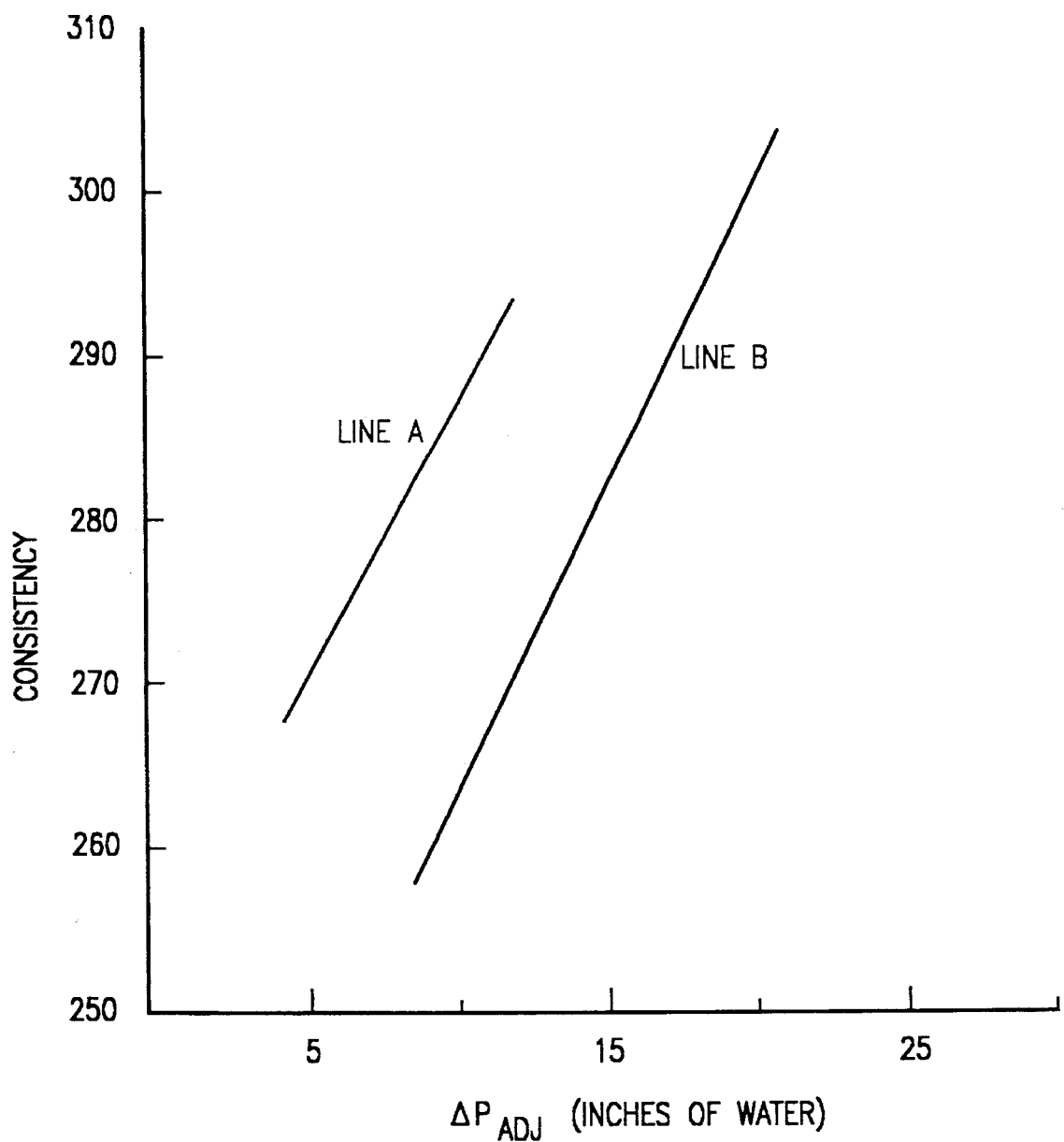
FIG. 3 is a graphical representation of the empirical relationship between the pressure drop and grease consistency.

Although the relationship between pressure drop and grease consistency can be modeled as shown by the curves in FIG. 3, it is not intended that the present invention replace laboratory testing. Such testing is still required to certify grease quality for customers and governmental regulations. The present invention provides a novel method and apparatus for monitoring and controlling a continuous grease making process for complex greases. It is suitable for maintaining such a process within desired parameters so as to minimize the amount of unusable product generated during start up.

Although the present invention has been described with preferred embodiments, it is to be understood that modifications and variations may be utilized without departing from the spirit and scope of this invention, as those skilled in the art will readily understand. Such modifications and variations are considered to be within the purview and scope of the appended claims.

What is claimed is:

1. A method of monitoring the consistency of a lubricating grease process stream comprising the steps of:

passing the grease process stream through the venturi so that a pressure drop occurs;

measuring the pressure drop using two axially separated pressure tap points along the venturi; and correlating the pressure drop to the consistency of the lubricating grease wherein the pressure drop is adjusted to ideal temperature and flow rate conditions according to the relationship $$\Delta P_{adj} = \Delta P + X_1(78+T) + X_2(R-100)$$

where $\Delta P_{adj}$ is the adjusted pressure drop, $\Delta P$ is the observed pressure drop, T is grease temperature, R is flow rate and $X_1$ and $X_2$ are production factors associated with a certain size venturi.

2. The method of claim 1 wherein the pressure drop occurs at constant temperature.

3. The method of claim 1 wherein the pressure drop occurs at constant flow rate.

4. The method of claim 1 wherein the pressure drop occurs at constant pressure into the venturi.

5. The method of claim 1 wherein the adjusted pressure drop is converted to an electronic signal.

6. The method of claim 5 wherein said electronic signal is displayed on a digital display.

7. The method of claim 5 wherein said electronic signal is monitored electronically for variation beyond a predetermined range, said variation causing the actuation of an alarm.

8. A method of monitoring the consistency of a lubricating grease process stream comprising the steps of:

passing the stream through a venturi so that a pressure drop occurs;

measuring the pressure drop using two axially separated pressure tap points along the venturi; and correlating the pressure drop to the consistency of the lubricating grease according to the relationship $$\Delta P_{adj} = \Delta P + X_1(78=T) + X_2(R-100)$$

where $\Delta P_{adj}$ is the adjusted pressure drop, $\Delta P$ is the observed pressure drop, T is grease temperature, R is flow rate and $X_1$ and $X_2$ are production factors associated with a certain size venturi, wherein the pressure drop occurs at constant temperature, flow rate and pressure into the venturi.

9. The method of claim 8 wherein the adjusted pressure drop is converted to an electronic signal.

10. The method of claim 9 wherein said electronic signal is displayed on a digital display.

11. The method of claim 10 wherein said electronic signal is monitored electronically for variation beyond a predetermined range, said variation causing the actuation of an alarm.

* * * * *